(12) United States Patent (10) Patent No.: US 6,747,021 B2
Corbett et al. (45) Date of Patent: Jun. 8, 2004

(54) CRYPTOPHYCIN COMPOUND

(75) Inventors: Thomas Hughes Corbett, Grosse Pointe Park, MI (US); Richard Elliott Moore, Honolulu, HI (US); Jian Liang, Honolulu, HI (US)

(73) Assignees: Eli Lilly and Company, Indianapolis, IN (US); Wayne State University, Detroit, MI (US); University of Hawaii, Honolulu, HI (US)

( * ) Notice: Subject to any disclaimer, the term of this patent is extended or adjusted under 35 U.S.C. 154(b) by 145 days.

(21) Appl. No.: 09/915,638

(22) Filed: Jul. 26, 2001

(65) Prior Publication Data

US 2002/0065261 A1 May 30, 2002

Related U.S. Application Data

(60) Provisional application No. 60/237,454, filed on Oct. 2, 2000.

(51) Int. Cl.⁷ .................... A61K 31/55; C07D 225/00
(52) U.S. Cl. .................................... 514/183; 540/451
(58) Field of Search ..................... 514/183; 540/451

(56) References Cited

U.S. PATENT DOCUMENTS

| 6,013,626 A | 1/2000 | Moore et al. ............... 514/9 |
| 6,180,679 B1 * | 1/2001 | Shih et al. ............... 514/619 |

FOREIGN PATENT DOCUMENTS

WO  WO 98/08505  3/1998

OTHER PUBLICATIONS

Chen B. et al, *Cellular Uptake of a Novel Cytotoxic Agent, Cryptophycin–52, By Human THP–1 Leukemia Cells and H–125 Lung Tumor Cells*, Int. J. Cancer (1998), 77, pp869–873.
Panda D. et al, Mechanism of Action of the Unusually Potent Microtubule Inhibitor Cryptophycin 1, Biochemisty (1997), 36, pp12948–12953.
Smith C. et al, Cryptophycin: A New Antimicrotubule Agent Active Against Drug–Resistant Cells, Cancer Research (Jul. 15, 1994), 54, pp3779–3784.
Wagner M. et al, In Vitro Pharmacology of Cryptophycin 52 (LY355703) in Human Tumor Cell Lines, Cancer Chemother. Pharmacol. (1999), 43, pp115–125.
Panda D. et al., *Antiproliferative mechanism of action of cryptophycin–52: Kinetic stabilization of microtubule dynamics by high–affinity binding to microtubule ends*, Proc. Natl. Acad. Sci. (Aug. 1998), 95:9313–9318.
Teicher B. et al., *Cryptophycin 52 and Cryptophycin 55 in Sequential and Simultaneous Combination Treatment Regimens in Human Tumor Xenografts*, In Vivo (2000), 14:471–480.
Moore R. et al., *The Search for New Antitumor Drugs from Blue–Green Algae*, Current Pharmaceutical Design (1996), 2:317–330.
Liang J. et al., *Synthesis of Cryptophycin 52 Using the Sharpless Asymmetric Dihydroxylation: Diol to Epoxide Transformation Optimized for a Base–Sensitive Substrate*, J. Org. Chem. (2000), 65:3143–3147.
Gardinier K. et al., *Enantiospecific Total Synthesis of the Potent Antitumor Macrolides Cryptophycins 1 and 8*, J. Org. Chem (1997), 62(21):7098–7099.
Norman B. et al., *Total Synthesis of Cryptophycin Analogues. Isosteric Replacement of the C–D Ester*, J. Org. Chem. (1998), 63(15):5288–5294.
Golakoti T. et al., *Structure Determination, Conformational Analysis, Chemical Stability Studies, and Antitumor Evaluation of the Cryptophycins. Isolation of 18 New Analogs from Nostoc sp. Strain GSV 224*, J. Am. Chem. Soc. (1995), 117:12030–12049.
Menon K. et al., *Antitumor activity of cryptophycins: effect of infusion time and combination studies*, Cancer Chemother. Pharmacol. (2000), 46:142–149.
Georg G. et al., *Halohydrin Analogues of Cryptophycin 1: Synthesis and Biological Activity*, Bioorganic & Medicinal Chemistry Letters 8 (1998), pp1959–1962.

* cited by examiner

Primary Examiner—Bruck Kifle
(74) Attorney, Agent, or Firm—Merchant & Gould P.C.

(57) ABSTRACT

The present invention provides antitumor methods, formulations, and compounds comprising a cryptophycin.

9 Claims, No Drawings

CRYPTOPHYCIN COMPOUND

This application claims the benefit of U.S. provisional application 60/237,454, filed Oct. 2, 2000.

FIELD OF THE INVENTION

This invention relates to the fields of pharmaceutical and organic chemistry and provides a cryptophycin compound useful in the treatment of cancer.

BACKGROUND OF THE INVENTION

Neoplastic diseases, characterized by the proliferation of cells not subject to the normal control of cell growth, are a major cause of death in humans and other mammals. Clinical experience in cancer chemotherapy has demonstrated that new and more effective drugs are desirable to treat these diseases. Such clinical experience has also demonstrated that drugs which disrupt the microtubule system of the cytoskeleton can be effective in inhibiting the proliferation of neoplastic cells.

The microtubule system of eukaryotic cells is a major component of the cytoskeleton and is in a state of dynamic assembly and disassembly. Heterodimers of tubulin are polymerized to form microtubules. Microtubules play a key role in the regulation of cell architecture, metabolism, and division. The dynamic state of microtubules is critical to their normal function. With respect to cell division, tubulin is polymerized into microtubules that form the mitotic spindle. The microtubules are then depolymerized when the mitotic spindle's use has been fulfilled. Accordingly, agents that disrupt the polymerization or depolymerization of microtubules, and thereby inhibit mitosis, comprise some of the most effective cancer chemotherapeutic agents in clinical use.

The cryptophycins are novel macrolides first isolated from blue-green algae (Nostoc sp. Strain GSV224) which have been shown to be potent tumor selective cytotoxins in vivo. Cryptophycins have been synthesized by a convergent method in which four fragments, Fragment A, Fragment B, Fragment C, and Fragment D (Golakati, et al., *Journal of the American Chemical Society*, 117(49), 12031 (1995)) are coupled together to form the final product (U.S. Pat. No. 6,013,626). Such methods have been used to prepare the original cryptophycins, isolated from Nostoc sp., as well as new cryptophycins.

Certain cryptophycin compounds, and methods for their preparation, are known in the literature. U.S. Pat. No. 4,845,085 and U.S. Pat. No. 4,845,086, for example, report novel semi-synthetic compounds formed by converting the epoxide of a particular cryptophycin to a carbon-carbon double bond. These compounds have potential as agents for mycotic infections.

U.S. Pat. No. 4,868,208 reports novel semi-synthetic antifungal compounds formed by subjecting a cryptophycin compound to hydrolysis or alcoholysis.

WO 95/17093, WO 96/39829, and WO 96/40184 report novel Cryptophycin compounds for inhibiting the proliferation of hyperproliferative cells.

WO 97/07798 reports a series of cryptophycin compounds that can be useful for disrupting the microtubulin system, as antineoplastic agents, as antifungals, and for the treatment of cancer.

WO 97/08334 reports novel cryptophycin compositions that exhibit a broad spectrum of antineoplastic activity similar to presently used antineoplastic agents such as vinblastine, taxol, and adriamycin.

WO 97/23211, WO 97/31632, WO 98/08506, WO 98/08505, and WO 98/08829 report novel cryptophycin compounds which can be useful for disrupting the microtubulin systems, as antineoplastic agents, and for the treatment of cancer.

Cryptophycin molecules are known to be somewhat toxic. Accordingly, it would be desirable to have cryptophycin molecules with lower toxicity that nonetheless retain the anti-cancer activity of the original cryptophycin molecules. Additionally, cryptophycin compounds having even greater solubility and stability are desired for most pharmaceutical uses. Surprisingly, applicants have now discovered the compound of this invention provides remarkably greater aqueous solubility as well as a superior ability to disrupt the microtubule system to any other compounds disclosed in WO 98/08505. This compound also has a lower toxicity than other cryptophycin molecules. Because of the lower toxicity, higher dosing levels may be achieved for a higher degree of cancer treatment.

As noted in WO 98/08505, such compounds can be prepared using total synthetic methods and are therefore well suited for development as pharmaceutically useful agents.

SUMMARY OF THE INVENTION

The present invention provides a compound of Formula I:

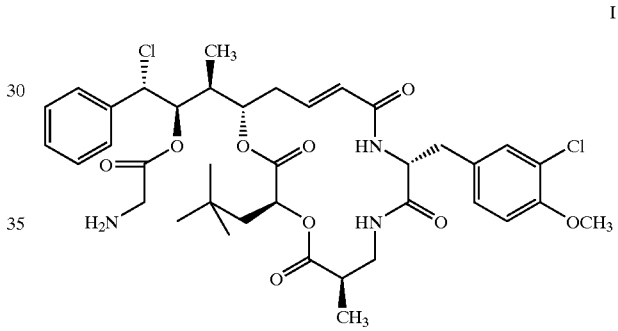

or a pharmaceutically acceptable salt thereof.

This invention also provides a pharmaceutical formulation that comprises, in association with a pharmaceutically acceptable carrier, diluent or excipient, a compound of Formula I.

The present invention provides a method for the treatment of hyperproliferative conditions such as cancer, neoplasm, and hyperproliferative cell growth in mammals comprising administering to a mammal in need of such treatment a pharmaceutically effective amount of the compound of Formula I or a pharmaceutically acceptable salt thereof.

Furthermore, the present invention provides a method for disrupting a microtubulin system in a mammal comprising administering to a mammal in need of such treatment an effective amount of a compound of Formula I.

This invention also provides the use of the compound of Formula I, or a pharmaceutically acceptable salt thereof, for the manufacture of a medicament for the treatment of hyperproliferative conditions such as cancer, neoplasm, and hyperproliferative cell growth in mammals. Additionally, this invention provides a pharmaceutical formulation adapted for the treatment of hyperproliferative conditions such as cancer, neoplasm, and hyperproliferative cell growth containing the compound of Formula I, or a pharmaceutically acceptable salt thereof.

This invention further provides the use of the compound of Formula I, or a pharmaceutically acceptable salt thereof, for the manufacture of a medicament for disrupting a microtubulin system. Additionally, this invention provides a pharmaceutical formulation adapted for disrupting a microtubulin system containing the compound of Formula I or a pharmaceutically acceptable salt thereof.

DETAILED DESCRIPTION OF THE INVENTION

The compound of Formula I is also known as Cryptophycin-309. We have found that Cryptophycin-309 exhibits lower toxicity than other cryptophycins but retains the anti-cancer activity of previously known cryptophycin molecules. Because of the lower toxicity, higher dosing levels may be achieved allowing for a higher degree of cancer treatment.

As used herein, the term "mammal" shall refer to the Mammalia class of higher vertebrates and includes, but is not limited to, a human. The term "treating" as used herein includes prophylaxis of the named condition or amelioration or elimination of the condition once it has been established. The compound of Formula I claimed herein can be useful for veterinary health purposes as well as for the treatment of a human patient.

The present invention provides methods for disrupting a microtubulin system in a mammal and for the treatment of hyperproliferative conditions such as cancer, neoplasm, and hyperproliferative cell growth in mammals by administering to a mammal in need of such treatment a pharmaceutically effective amount of a compound of Formula I. The preferred mammal is human.

Because the compound of Formula I is an amine, it is basic in nature and accordingly reacts with any of a number of inorganic and organic acids to form pharmaceutically acceptable acid addition salts. It is preferable to convert the free amine to a pharmaceutically acceptable acid addition salt for ease of handling and administration. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogen-phosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxy-benzoate, methoxybenzoate, phthalate, sulfonate, xylenesulfonate, phenylacetate, phenylpropionate, phenylbutyrate, citrate, lactate, α-hydroxybutyrate, glycollate, tartrate, methanesulfonate, propanesulfonate, naphthalene-1-sulfonate, naphthalene-2-sulfonate, mandelate and the like. A preferred pharmaceutically acceptable salt is the hydrochloride salt.

Cryptophycin-309, the compound of Formula I, may be prepared from Cryptophycin-292 by methods well known to the skilled artisan as illustrated in Scheme I:

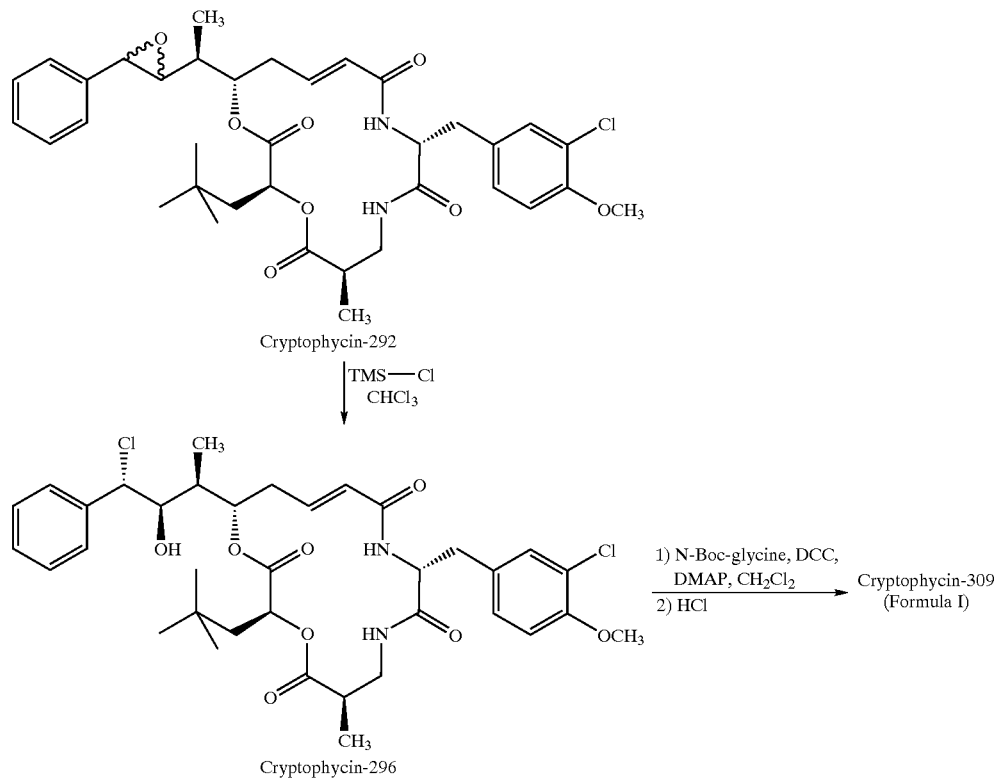

The transformation of the epoxide to the chlorohydrin is accomplished generally by the procedure described in U.S. Pat. No. 6,252,064, incorporated herein by reference. Briefly, the epoxide, Cryptophycin-292, is treated with trimethylsilyl chloride in a suitable solvent, typically chloroform, at reduced temperature, typically about −63° C., to provide, after silica gel chromatography, the chlorohydrin Cryptophycin-296. This resulting chlorohydrin is then coupled under standard conditions with N-(tert-butoxycarbonyl)glycine to form the corresponding ester. The N-(tert-butoxycarbonyl) substituent is removed by treatment with a suitable acid, typically hydrogen chloride or hydrochloric acid, to provide the compound of Formula I.

Cryptophycin-292 may be prepared by general methods for synthesizing cryptophycin molecules well known in the art. Cryptophycin molecules have typically been synthesized by a convergent synthesis in which four (4) subunits are assembled. The combined AB-subunit has the following formula:

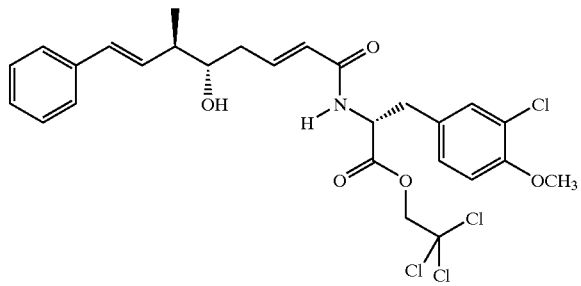

II

The preparation of this AB-subunit is well known in the art (See: WO 98/09955, WO 98/08505, and WO 00/23429).

The C-subunit, β-alanine, has the following formula:

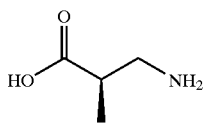

III and is commercially available in a protected form, or may be prepared as described by Barrow, et al. (*Journal of the American Chemical Society*, 117(9), 2479–2490 (1995)) by White, et al., (*Journal of Organic Chemistry*, 64(7), 6206–6216 (1999)), or in EP 1 059 286 A1.

The D-subunit, 2(S)-(−)-4,4-dimethyl-2-hydroxypentanoic acid, has the following formula:

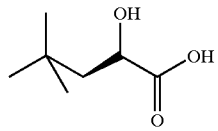

IV and may be prepared as described in the following scheme.

Scheme II

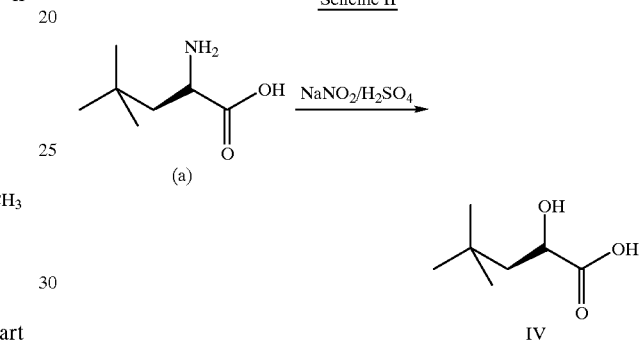

Briefly, a solution of L-neopentylglycine (a) in sulfuric acid is treated with sodium nitrite to provide the compound of Formula IV.

Alternatively, a protected form of the compound of Formula IV may be prepared as described in Scheme III.

Scheme III

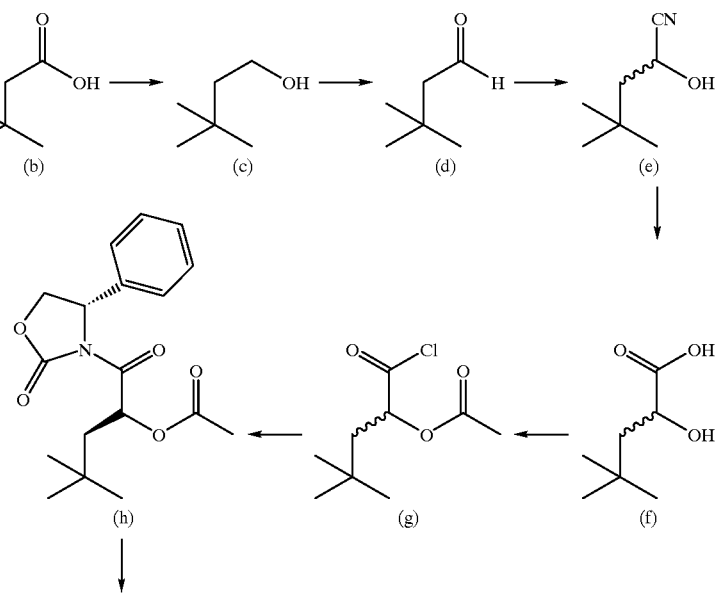

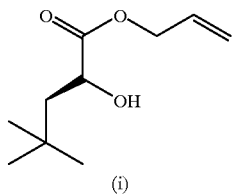

(i)

Tert-butylacetic acid (b) is reduced with a hydride reducing agent, preferably lithium aluminum hydride, to provide 3,3-dimethyl-1-butanol (c). Oxidation of alcohol (c) with 2,2,6,6-tetramethyl-1-piperidinyloxy, free radical (TEMPO), provides 3,3-dimethylbutyraldehyde (d), which is isolated by co-distillation with tetrachloroethane. Aldehyde (d) is treated sequentially with trimethylsilyl cyanide and a catalytic amount of zinc iodide, followed by methanol to afford (±)-4,4-dimethyl-2-hydroxypentanenitrile (e). This nitrile is hydrolyzed first with hydrochloric acid, followed by 50% NaOH to provide racemic pentanoic acid (f). Sequential treatment of racemate (f) with neat acetyl chloride, followed by either oxalyl chloride or thionyl chloride and N,N-dimethylformamide, provides 4,4-dimethyl-2-acetoxypentanoyl chloride (g), which is then coupled with (R)-(−)-4-phenyl-2-oxazolidinone in the presence of 4-dimethylaminopyridine and N,N-diisopropylethylamine in dichloromethane to give a mixture of the acetoxy diastereomers. This diastereomeric mixture of acetates is separated by column chromatography to provide the single diastereomeric acetate (h). The acetate (h) is treated with sodium hydroxide in a solution of tetrahydrofuran/methanol/water to give the desired (2S)-(−)-4,4-dimethyl-2-hydroxypentanoic acid IV. The crude pentanoic acid IV is converted to an ester, preferably the allyl ester, and is then purified by chromatography to provide allyl (2S)-(−)-4,4-dimethyl-2-hydroxypentanoate (i).

Cryptophycin-292 is assembled from these subunits as illustrated in the following scheme.

Scheme IV

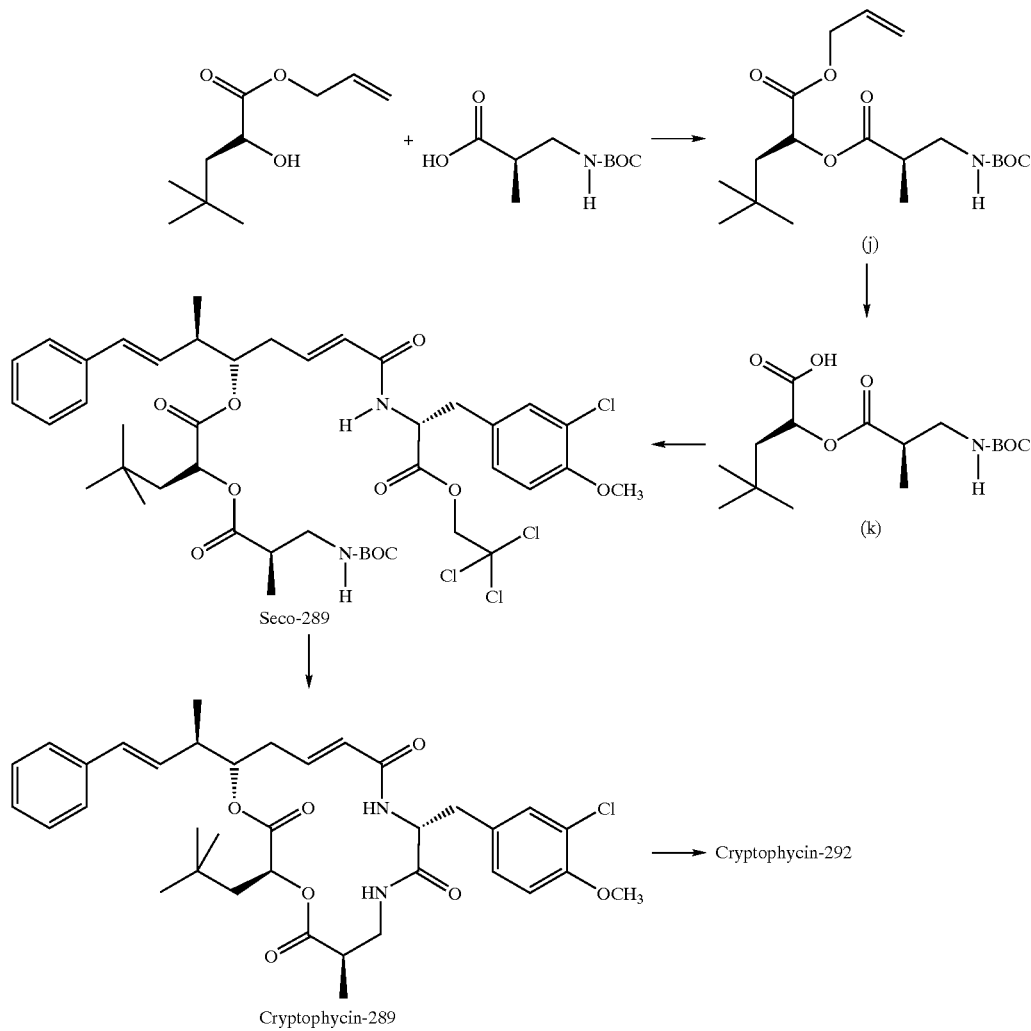

Coupling of allyl ester (i) with the N-tert-butoxycarbonyl derivative of the C-subunit is accomplished by reaction of the two components in the presence of dicyclohexylcarbodiimide and dimethylaminopyridine in dichloromethane, providing the allyl ester of the CD-subunit (j). The allyl protecting group is removed with morpholine in the presence of tetrakis(triphenylphosphine)palladium(O) in tetrahydrofuran furan to afford the CD-subunit (k), which is then coupled with the AB-subunit (II) in the presence of dicyclohexylcarbodiimide and dimethylaminopyridine in dichloromethane to provide Seco-289. Deprotection of Seco-289 is accomplished by sequential treatment with trifluoroacetic acid and $K_2CO_3$. Cyclization of Seco-289 is accomplished by reaction with 2-hydroxypyridine in toluene to provide Cryptophycin-289. Epoxide formation is performed by reaction with 3-chloroperoxybenzoic acid at room temperature to provide Cryptophycin-292.

Preparation I

2(S)-(-)-4,4-dimethyl-2-hydroxypentanoic Acid (D-subunit)

To a solution of L-neopentylglycine (2.9 gm, 20 mMol) in 1.0 N sulfuric acid (55 mL) is added slowly sodium nitrite (2.76 gm, 40 mMol) at 0° C. The mixture is stirred vigorously overnight and is allowed to warm to room temperature. Ethyl acetate (25 mL) is added and the phases are separated. The aqueous phase is extracted with ethyl acetate (2×80 mL). The combined organic phases are washed with 0.5 N hydrochloric acid, dried, and concentrated to provide 2.3 gm (79%) of the desired compound as a colorless wax. The aqueous phase was treated with additional 1.0 N sulfuric acid (8 mL) and sodium nitrite (2.76 gm) to provide an additional 0.5 gm of the title compound.

$[\alpha]_D$ ($CHCl_3$)=−6.0° (c=5.0)

$^1$H-NMR (300 MHz, $CDCl_3$): δ4.33 (dd, J=9.5, 2.2, 2H), 1.81 (dd, J=2.4, 14.6, 3H), 1.53 (dd, J=9.3, 14.6, 2H), 1.02 (s, 5H).

Preparation II

Alternate Synthesis of 2(S)-(-)-4,4-dimethyl-2-hydroxypentanoic Acid (D-subunit)

A. 3,3-Dimethyl-1-butanol (c)

A mechanically stirred suspension of lithium aluminum hydride (33.5 g, 0.883 mol) is prepared in diethyl ether (1 L, anhydrous) under nitrogen and cooled to 0° C. To this suspension is added tert-butylacetic acid (b) in diethyl ether (500 mL) dropwise, and at such a rate as to keep the contents in the flask (3 hours). After complete addition, the ice bath is removed and the suspension stirred overnight at room temperature. The mixture is again cooled to 0° C. and the reaction quenched by the slow addition of water (200 mL), followed by hydrochloric acid (12 N, 100 mL). The organic layer is decanted away from the aluminum salts and the salts are washed with diethyl ether (500 mL). The combined organic layers are washed with hydrochloric acid (1 N, 500 mL), sodium bicarbonate (saturated aqueous, 500 mL), sodium chloride (saturated aqueous, 500 mL), dried (magnesium sulfate), filtered, and the filtrate evaporated (40° C., 20 mm Hg). The residue is distilled through a 140 mm Vigreaux column (bp 140–150° C., 760 mm Hg under $N_2$) to provide the desired compound as a colorless oil, 74.6 g (85%).

$^1$H NMR ($CDCl_3$) δ3.73 (t, J=7.6 Hz, 2H), 1.55 (t, J=7.6 Hz, 2H), 1.3 (bs, 1H), 0.96 (s, 9H).

B. (±)-4,4-Dimethyl-2-hydroxypentanenitrile (e)

A mechanically stirred solution of 3,3-dimethyl-1-butanol (c) (74.6 g, 0.730 mol) is prepared in 1,1,2,2-tetrachloroethane (400 mL) and water (2.5 L). The partition is stirred vigorously and treated sequentially with sodium bicarbonate (111 g, 1.32 mol), potassium carbonate (18.5 g, 0.134 mol), TEMPO (5.00 g, 0.032 mol), tetrabutylammonium chloride (20.1 g, 0.0723 mol), and N-chlorosuccinimide (110.7 g, 0.829 mol). After stirring overnight at room temperature, the layers are separated and the organic layer washed with hydrochloric acid (1 N, 200 mL), sodium bicarbonate (saturated aqueous, 200 mL), sodium chloride (saturated aqueous, 200 mL), dried (magnesium sulfate), and filtered. The filtrate is distilled through a 140 mm Vigreaux column (b.p 140–150° C., 760 mm Hg under $N_2$) to provide a solution of 3,3-dimethylbutyraldehyde (d) in 1,1,2,2-tetrachloroethane (616 g total weight). $^1$H NMR shows the solution to be about 8.9% by weight aldehyde, approximately 55 g (77%). The solution is cooled to 0° C., stirred, and treated sequentially with zinc iodide (3.00 g, 9.40 mmol), and trimethylsilyl cyanide (83.0 mL, 0.622 mol) dropwise, over a 30 minute period. The ice bath is removed and the solution is stirred at room temperature for 2 hours. Methanol (50 mL, 1.23 mol) is added dropwise (10 min) and stirring is continued for 1 hour. The solution is washed once with water, then evaporated (40° C., 20 mm Hg, two 100 mL portions of water are added to azeotrope with 1,1,2,2-tetrachloroethane during evaporation) to provide 70 g (±)-4,4-dimethyl-2-hydroxypentanenitrile (e) as a reddish oil (75%).

$^1$H NMR ($CDCl_3$) δ4.58 (t, J=1.2 Hz, 1H), 2.5 (bs, 1H), 1.9 (m, 2H), 1.05 (s, 9H).

C. (±)-4,4-Dimethyl-2-hydroxypentanoic Acid (f)

A solution of 4,4-dimethyl-2-hydroxypentanenitrile (f) (70.0 g, 0.550 mol) is prepared in hydrochloric acid (12 N, 150 mL, 1.80 mol, the solution immediately refluxes) and is stirred overnight at room temperature. The resulting thick slurry is diluted with diethyl ether (500 mL) and 1:1 saturated aqueous sodium chloride/water (500 mL). The layers are separated and the aqueous layer extracted with diethyl ether (200 mL). The combined organic layers are evaporated (40° C., 20 mm Hg) and the residue stirred in water (200 mL), treated with sodium hydroxide (50% solution in water, 50.0 g, 0.625 mol), and heated to 80° C. for 2 h. The heat is removed and the solution poured into cracked ice (ca. 500 g) containing hydrochloric acid (12 N, 70 mL, 0.84 mol). This aqueous suspension is extracted with diethyl ether (2×500 mL), and the combined extracts are dried (magnesium sulfate), filtered, and the filtrate evaporated (40° C., 20 mm Hg) to provide 67 g (83%) (±)-4,4-dimethyl-2-hydroxypentanoic acid (f) as a colorless solid.

mp=72–73° C.

MS(FIA): m/e (% relative intensity) 145.1 ($M^+$−1, 100).

EA: Calculated $C_7H_{14}O_3$ (146.18): C, 57.51; H, 9.65. Found: C, 57.75; H, 9.34.

D. (4R,2'S)-(-)-3-(4',4'-Dimethyl-2'-acetoxypentanoyl)-4-phenyloxazolindin-2-one (h)

A solution of (±)-4,4-dimethyl-2-hydroxypentanoic acid (f) (40.0 g, 0.274 mol) is prepared in acetyl chloride (70.0 mL, 0.984 mol) and stirred at room temperature for 2 hours. The solution is concentrated (40° C., 20 mm Hg), the residue dissolved in dichloromethane (300 mL), and treated sequentially with oxalyl chloride (30.0 mL, 0.344 mol) and dimethylformamide (0.2 mL, 3 mmol). After stirring overnight at room temperature, the solution is concentrated (40° C., 20 mm Hg), stirred in dichloromethane (400 mL), and treated with N,N-diisopropylethylamine (120 mL, 0.689 mol), dimethylaminopyridine (0.50 g, 4.1 mmol), and (R)-(-)-4-phenyl-2-oxazolidinone (50.0 g, 0.306 mol), resulting in a gentle reflux. After stirring overnight at room temperature, the mixture is washed with hydrochloric acid (1 N, 2×500 mL). The aqueous layer is extracted with dichloromethane (100 mL) and the organic layers are washed with sodium chloride (saturated aqueous, 200 mL), dried (magnesium sulfate), filtered, and the filtrate evaporated (40° C., 20 mm Hg) to provide 100 g of the crude diastereomers as a paste. The paste is divided into two 50 g portions and chromatographed on silica gel [1 kg, 100 mm column, 4:1:1 tert-butyl methyl ether/dichloromethane/hexanes] to provide 42.5 g of oxizolidinone (h) as a colorless solid (47%). An analytical sample is prepared by recrystallizing 0.78 g from 40 mL of 1:1 ′BuOMe/hexanes to afford 0.61 g of pure (h) as white needles.

mp=148–149° C.

$[\alpha]_D^{25}=-123.6°$ (c=1.03, $CHCl_3$)

MS(FIA): m/e (% relative intensity) 351.0 (50), 334.2 ($M^+$+1, 70), 274.0 (100).

EA: Calculated. for $C_{18}H_{23}NO_5$ (333.38): C, 64.85; H, 6.95; N, 4.20. Found: C, 65.08; H, 7.04; N, 4.28.

(4R,2′R)-(−)-3-(4′,4′-Dimethyl-2′-acetoxypentanoyl)-4-phenyloxazolindin-2-one

The column above provides 40.0 g of a white solid, which is recrystallized from 5:2 ′BuOMe/hexanes (350 mL total) to afford 30.0 g (33%) of the opposite isomer of oxizolidinone (h) as fine, white needles.

mp=140–141° C.

$[\alpha]_D^{25}=-80.50°$ (c=1.00, $CHCl_3$)

MS(FIA): m/e (% relative intensity) 392.2 (20), 351.5 (30), 334.1 ($M^+$+1, 50), 274.3 (100).

EA: Calculated for $C_{18}H_{23}NO_5$ (333.38): C, 64.85; H, 6.95; N, 4.20. Found: C, 65.15; H, 6.97; N, 4.43.

E. Allyl (2S)-(−)-4,4-Dimethyl-2-hydroxypentanoate (i)

A solution of (4R,2′S)-(−)-3-(4′,4′-dimethyl-2′-acetoxypentanoyl)-4-phenyloxazolindin-2-one (h) (42.5 g, 0.127 mol) is prepared in tetrahydrofuran (750 mL), $CH_3OH$ (350 mL), and water (350 mL) and treated with sodium hydroxide (25 g of a 50% solution in water, 0.313 mol). After stirring overnight at rt, the mixture is concentrated (20° C., 20 mm Hg) to about ¼ volume, diluted with diethyl ether (500 mL), treated with hydrochloric acid (12 N, 30 mL, 0.36 mol) and sodium chloride (50 g), and stirred for 15 minutes. The layers are separated and the aqueous layer extracted with diethyl ether (2×500 mL). The organic layers are concentrated (40° C., 20 mm Hg) and the residue stirred in water (250 mL) and treated with sodium bicarbonate (20.0 g, 0.200 mol) and tetrabutylammonium bromide (46.0 g, 0.142 mol). The mixture was heated to 45° C., stirred, and treated with allyl bromide (31.4 g, 0.260 mol), neat, over a 6 hour period. Stirring is continued at 45° C. for 2 hours after complete addition and then at room temperature overnight. Hexanes (200 mL) are added and the mixture is made strongly acidic with hydrochloric acid (3 N, 100 mL). The layers are separated and the aqueous layer extracted with hexanes (200 mL). The organic layers are washed with hydrochloric acid (1 N, 100 mL), sodium chloride (saturated aqueous, 200 mL), dried (magnesium sulfate), filtered, and the filtrate evaporated (40° C., 20 mm Hg) to provide 16.8 g of an amber oil. The oil is chromatographed on $SiO_2$ (70×160 mm column, 15% ′BuOMe in hexanes) to provide 14.4 g of (i) (61%).

$[\alpha]_D^{25}=-6.320$ (c=1.17, $CHCl_3$)

MS (FD+) m/e (% relative intensity) 186.1 ($M^+$, 100).

Preparation III (2S,2′R)-(−)-2-[3′-[[(tert-Butoxycarbonyl)amino]-2′-methylpropanoyl]oxy]-4,4-dimethylpentanoic Acid (k), (CD-subunit)

A. Coupling

A solution of (R)-3-[(tert-butoxycarbonyl)amino]-2-methylpropanoic acid (16.0 g, 0.789 mol) and allyl (2S)-(−)-4,4-dimethyl-2-hydroxypentanoate (i) (14.0 g, 0.0752 mol) is prepared in dichloromethane (100 mL, anhydrous) under nitrogen and treated with dimethylaminopyridine (0.50 g, 4.1 mmol). The solution is stirred, cooled to 0° C., and treated with dicyclohexylcarbodiimide (22.1 g, 0.107 mol) in dichloromethane (100 mL, anhydrous) dropwise and at such a rate as to keep the temperature at or below +10° C. The ice bath is removed and the mixture stirred for 4 hours. The mixture is filtered, concentrated (20° C., 20 mm Hg), and the residue chromatographed on silica gel (1 kg, 100 mm diameter column, 15% ′BuOMe in hexanes) to provide 28.8 g of allyl (2S,2′R)-(−)-2-[3′-[[(tert-butoxycarbonyl)amino]-2′-methylpropanoyl]oxy]-4,4-dimethylpentanoate (j) as a colorless oil in quantitative yield.

$[\alpha]_D^{25}=-45.4°$ (c=0.99, $CHCl_3$)

MS(FIA): m/e (% relative intensity) 372.3 ($M^+$+1, 37), 316.1 (25), 272.4 (100).

B. Deesterification

A solution of pentanoate (j) (24.4 g, 65.7 mmol) is prepared in tetrahydrofuran (300 mL, anhydrous) and stirred under nitrogen. The solution is treated sequentially with morpholine (65.0 g, 0.746 mol) and tetrakis (triphenylphosphine) palladium(O) (320 mg, 0.276 mmol), then stirred for 3.5 hours. The mixture is diluted with diethyl ether (500 mL) and washed with hydrochloric acid (250 mL of 3 N, followed by 250 mL of 1 N). The aqueous layers are extracted with diethyl ether (200 mL), and the combined organic layers are washed with sodium chloride (saturated aqueous, 200 mL), dried (magnesium sulfate), filtered, and the filtrate evaporated (40° C., 20 mm Hg) to provide 22.2 g of the title compound as a yellow paste in quantitative yield.

$[\alpha]_D^{25}=-40.9°$ (c=1.09, $CHCl_3$)

MS(FIA): m/e (% relative intensity) 332.2 ($M^+$+1, 10), 276.2 (15), 232.2 (100).

Preparation IV

Alternate Synthesis of (2S,2′R)-(−)-2-[3′-[[(tert-Butoxycarbonyl)amino]-2′-methylpropanoyl]oxy]-4,4-dimethylpentanoic Acid (k), (CD-subunit)

A solution of (R)-3-[(tert-butoxycarbonyl)amino]-2-methylpropanoic acid N-hydroxysuccinimide ester (0.30 g, 1.0 mmol) and (2S)-(−)-4,4-dimethyl-2-hydroxypentanoic acid (IV) (0.219 g, 1.5 mmol) is prepared in acetonitrile (10 mL, anhydrous) and treated with dimethylaminopyridine (0.525 g, 4.3 mmol). After stirring for 18 hours, the acetonitrile is removed by evaporation. The residue is treated with hydrochloric acid (0.1 M) and the resulting mixture is extracted with ethyl acetate (2×50 mL). The organic phases are combined, dried, and concentrated. The residue is chromatographed (C18 reversed-phase column, YMC ODS gel), eluting with 1:1 methanol:water followed by methanol to give 0.268 gm (81%) of the title compound as a colorless wax.

$[\alpha]_D^{25}=-37.5°$ (c=1.4, $CHCl_3$)

MS(FAB): m/e (% relative intensity) 354 ($M^+$+Na, 100), 298 (11.8), 276 (7.2), 232 (9.6), 130 (8.1).

MS(HRFAB): m/e=354.1878 (Calculated for $C_{16}H_{29}NO_6$: 354.1893).

EXAMPLE 1

Cryptophycin-309 Hydrochloride

A. Seco-289

A solution of AB-subunit (II) (40.0 g, 67.9 mmol) and CD-subunit (k) (21.8 g, 65.8 mmol) is prepared and stirred in dichloromethane (800 mL, anhydrous) under nitrogen, cooled to 0° C., and treated sequentially with dicyclohexylcarbodiimide (23.7 g, 115 mmol) and dimethylaminopyridine (3.0 g, 25 mmol). After stirring overnight at room temperature, the mixture is filtered through celite, concentrated to ¼ volume (40° C., 20 mm Hg), and chromatographed on silica gel (1 kg, 100 mm diameter column, 1:2:4 $^t$BuOMe/dichloromethane/hexanes) to provide 41.5 g of a white solid. The solid is recrystallized from $^t$BuOMe (two crops; second from $^t$BuOMe/hexanes) to afford 37.0 g of Seco-289 as white crystals (62%).

mp=95–115° C.

$[\alpha]_D^{25}$=−5.51° (c=1.03, CHCl$_3$)

MS(FIA): m/e (% relative intensity) 905.6 (51), 904.6 (51), 903.6 (100), 902.8 (M$^+$, 41), 901.7 (95).

B. Cryptophycin 289

A solution of Seco-289 (30.3 g, 33.6 mmol) in dichloromethane (100 mL) is stirred at 0° C. and treated with trifluoroacetic acid (90.0 mL, 1.17 mol), neat, at such a rate as to keep the temperature at or below +8° C. (about 10 min). After 2 hours the solution is concentrated (20° C., 20 mm Hg), then poured into a mechanically stirred mixture of $^t$BuOMe (400 mL) and cracked ice/water (400 g) containing potassium carbonate (150 g, 1.09 mol). The mixture is stirred rapidly for 30 min, the layers are separated, and the aqueous layer extracted with $^t$BuOMe (400 mL). The organic layers were washed with water (400 mL), sodium chloride (saturated aqueous, 400 mL), dried (magnesium sulfate), filtered, and the filtrate evaporated (40° C., 20 mm Hg). The residue is stirred in toluene (2 L) and treated with 2-hydroxypyridine (12.9 g, 136 mmol). After stirring overnight at room temperature, the mixture is treated with sodium bicarbonate (saturated aqueous, 500 mL) and stirred for 30 minutes. The layers are separated and the organic layer dried (magnesium sulfate) (500 mL of dichloromethane are added during drying to ensure good recovery), filtered, and the filtrate evaporated to 24 g of a yellow foam. The foam is chromatographed on silica gel (70×230 mm column, 2:1:1 $^t$BuOMe/CH$_2$Cl$_2$/hexanes) to provide a white solid, which is recrystallized from $^t$BuOMe/hexanes to provide 13.4 g of Cryptophycin 289 as colorless crystals (61%).

mp=209–210° C.

$[\alpha]_D^{25}$=+46.2° (c=1.00, CHCl$_3$)

MS(FIA): m/e (% relative intensity) 653.3 (100).

EA: Calculated for C$_{36}$H$_{45}$ClN$_2$O$_7$ (653.21): C, 66.20; H, 6.94; N, 4.29. Found: C, 66.42; H, 6.95; N, 4.16.

C. Cryptophycin 296

A solution of Cryptophycin 289 (13.2 g, 20.2 mmol) in chloroform (43 mL) is stirred and treated with m-chloroperbenzoic acid (m-CPBA) (95% pure, 5.19 g, 30.1 mmol). After stirring overnight at room temperature, the solution is diluted with chloroform until clear, washed with sodium bicarbonate (saturated aqueous, 100 mL), sodium sulfite (saturated aqueous, 100 mL), sodium chloride (saturated aqueous, 100 mL), dried (magnesium sulfate), filtered, and the filtrate evaporated (40° C., 20 mm Hg) to provide 14 g of the Cryptophycin-292 as a mixture of epoxide isomers, as a white foam. The foam is dissolved in chloroform, cooled to −63° C., and treated with chlorotrimethylsilane (23.5 mL, 185 mmol) via syringe. The mixture is stirred at −63° C. for 5 hours, then allowed to stand in the freezer at −20° C. overnight. The mixture is again cooled to −63° C. and treated with sodium bicarbonate (saturated aqueous, 60 mL) with vigorous stirring. The cold bath is removed and the mixture allowed to warm to room temperature over a 1 hour period. The layers are separated and the aqueous layer extracted with chloroform. The organic layers are washed with sodium bicarbonate (saturated aqueous, 60 mL), sodium chloride (saturated aqueous, 100 mL), dried (magnesium sulfate), filtered, and the filtrate evaporated to 14 g of a white residue. The residue is chromatographed on silica gel (70×160 mm of silica gel, packed and eluted in 2:1:1 $^t$BuOMe/CH$_2$Cl$_2$/hexanes) to provide 4.51 g of Cryptophycin 296 as a colorless foam (32%)

$[\alpha]_D^{20}$=+56.2° (c=0.97, CHCl$_3$)

MS(FIA): m/e (% relative intensity) 707.4 (100), 705.3 (95).

D. Glycinate Ester Formation

A solution of Cryptophycin-296 (2.00 g, 2.83 mmol), N-[tert-butoxycarbonyl]glycine (745 mg, 4.25 mmol), and dimethylaminopyridine (34 mg, 0.28 mmol) is prepared and stirred in dichloromethane (10 mL, anhydrous) under nitrogen, and treated with dicyclohexylcarbodiimide (877 mg, 4.25 mmol). After stirring 1 hour at room temperature, the mixture is diluted with ethyl acetate/hexanes (15 mL, 3:1) and filtered through celite (the pad is washed with 30 mL of 3:1 ethyl acetate/hexanes). The filtrate is concentrated (40° C., 20 mm Hg) to provide 2.72 g of white foam. The foam is chromatographed on silica gel (150 g, packed and eluted in 3:1 ethyl acetate/hexanes) to provide 2.22 g of N-[tert-butoxycarbonyl]-Cryptophycin-309 as a colorless foam. The foam is dissolved and stirred in dichloromethane (12 mL, anhydrous) and treated with hydrogen chloride (3.4 mL of a 3.3 M solution in dioxane, 11 mmol). After stirring for 2 hours at room temperature, the solution is concentrated (40° C., 20 mm Hg), slurried in ethyl acetate (50 mL) and concentrated again (40° C., 20 mm Hg, 6 h), then stored under vacuum (0.1 mm Hg) for 18 h to provide 1.92 g of the title compound as a white solid (85%).

$[\alpha]_D^{20}$=+56.2° (c 0.97, CHCl$_3$)

$^1$H NMR (CD$_3$OD) δ7.4 (m, 5H), 7.21 (dd, J=8.5, 2.0 Hz, 1H), 7.01 (d, J=8.6 Hz, 1H), 6.67 (ddd, J=15.1, 11.2, 3.8 Hz, 1H), 5.98 (d, J=15.1 Hz, 1H), 5.56 (d, J=9.8 Hz, 1H), 5.18 (d, J=10.8 Hz, 1H), 5.17 (d, J=9.9 Hz, 1H), 4.54 (dd, J=11.1, 3.9 Hz, 1H), 3.87 (s, 3H), 3.79 (d, J=17.6 Hz, 1H), 3.62 (ddd, J=16.7, 9.3, 3.0 Hz, 1H), 3.3 (m, 3H), 3.2 (m, 2H), 2.7 (m, 4H), 2.3 (m, 1H), 2.0 (m, 1H), 1.9 (m, 1H), 1.23 (d, J=7.5 Hz, 3H), 1.12 (d, J=7.0, 3H), 1.07 (s, 9H).

$^{13}$C NMR (CD$_3$OD) δ177.7, 174.5, 172.5, 168.7, 168.1, 155.8, 143.8, 139.4, 132.7, 131.9, 130.7, 130.1, 129.8, 129.6, 125.8, 123.7, 114.0, 78.4, 76.5, 72.5, 61.4, 58.0, 57.1, 45.6, 41.6, 40.8, 40.1, 39.7, 38.4, 36,7, 31.9, 30.5, 15.6, 10.1.

IR (KBr) $v_{max}$ 2962, 1758, 1729, 1674, 1527, 1503, 1258, 1230, 1177, 1066 cm$^{-1}$ MS(ESI+): m/e (% relative intensity) 765.5 (34), 764.5 (100), 763.5 (43), 762.5 (76).

EXAMPLE 2

Alternate Synthesis of Cryptophycin-309

A. Seco-289

A solution of AB-subunit (II) (64 mg, 0.109 mmol), CD-subunit (k) (38 mg, 0.115 mmol), dimethylaminopyridine (12 mg, 0.1 mmol), and 1-(3-dimethylaminopropyl)-3-ethylcarbodiimide hydrochloride (53 mg, 0.276 mmol) is prepared and stirred in acetonitrile (1 mL, anhydrous). After stirring overnight at room temperature, the mixture is diluted with ethyl acetate and is washed sequentially with 0.1 N hydrochloric acid, sodium bicarbonate (saturated aqueous) and sodium chloride (saturated aqueous). The combined aqueous layers are extracted with ethyl acetate. The organic layers are combined, dried and concentrated to provide a light yellow solid. The solid is recrystallized from ethyl acetate/hexanes to provide 76 mg (78%) of the desired product as a crystalline solid.

$[\alpha]_D^{25}$=−5.3° (c 2.3, $CHCl_3$)

FABMS: m/e (% relative intensity) 903 (8.9), 803 (100), 767 (4.2) 625 (5.1), 344 (9.8), 902.8 ($M^+$, 41), 901.7 (95).

MS(HRFAB): m/e=901.2777 (Calculated for $C_{43}H_{57}N_2O_{10}Cl_4$: 901.2767).

EA: Calculated for $C_{43}H_{57}N_2O_{10}Cl_4$: C, 57.21; H, 6.25; N, 3.10. Found: C, 57.07; H, 6.26; N, 2.97.

B. Cryptophycin 289

Seco-289 (670 mg, 0.74 mmol) is dissolved in trifluoroacetic acid (8 mL) at 0° C. After 30 minutes the solution is concentrated and the residue dissolved in ethyl acetate. This solution is washed successively with sodium carbonate (10% aqueous) and sodium chloride (saturated aqueous). The combined aqueous phases are extracted with ethyl acetate. The ethyl acetate phases are combined, dried, and concentrated to a yellow foam. This material is dissolved in toluene (30 mL) and treated with 2-hydroxypyridine (352 mg, 3.7 mmol). After stirring overnight at room temperature, the mixture is diluted with ethyl acetate and is washed with water (2×60 mL), dried, and evaporated. The residue is dissolved in dichloromethane and is subjected to silica gel chromatography, eluting with 1:1 ethyl acetate/hexanes. The recovered product is recrystallized to provide 265 mg of the desired compound as small needles (55%).

$[\alpha]_D^{25}$=+41.3° (c=5.5, $CHCl_3$)

MS(FAB): m/e (% relative intensity) 653 (100).

MS(HRFAB): m/e 653.2955 (Calculated for $C_{36}H_{46}ClN_2O_7$: 653.2994).

C. Cryptophycin-292 (β-epoxide)

A solution of Cryptophycin-289 (93 mg, 0.14 mmol) in dichloromethane (7 mL) is stirred and treated with m-chloroperbenzoic acid (m-CPBA) (120 mg, 0.70 mmol) at 0° C. After stirring overnight at room temperature, the solution is concentrated and the residue subjected to silica gel chromatography, eluting with 1:1 ethyl acetate/hexanes. Separation of the α- and β-epoxides is achieved by reversed-phase HPLC (C18, 3:1 acetonitrile/water) to provide 48 mg (50%) of the desired compound as an amorphous solid.

$[\alpha]_D^{25}$=+28.5° (c=2.7, $CHCl_3$)

MS(FAB): m/e (% relative intensity) 669 (100).

MS(HRFAB): m/e=669.2956 (Calculated for $C_{36}H_{46}ClN_2O_8$: 669.2943).

D. Cryptophycin-296

A solution of Cryptophycin-292 (32 mg, 0.050 mmol) in chloroform (3 mL) is prepared and to this solution is added a solution of chlorotrimethylsilane in dichloromethane (1.0 M, 0.75 mL, 0.75 mmol) at −60° C. The clear solution is stirred for 30 minutes and is concentrated. The residue is purified by silica gel chromatography, eluting with 1:1 ethyl acetate/hexanes to provide 32 mg (91%) of the desired compound.

$[\alpha]_D^{20}$=+49.3° (c=3.0, $CHCl_3$)

MS(FAB): m/e (% relative intensity) 705 (3.3), 364 (4.0), 231 (15.5), 117 (100).

MS(HRFAB): m/e=705.2686 (Calculated for $C_{36}H_{47}Cl_2N_2O_8$: 705.2686).

E. Glycinate Ester Formation

A solution of Cryptophycin-296 (10.0 mg, 0.014 mmol), N-[tert-butoxycarbonyl]glycine (12.4 mg, 0.071 mmol), and dimethylaminopyridine (0.17 mg, 0.0014 mmol) is prepared and stirred in dichloromethane (100 μL). To this mixture is added dicyclohexylcarbodiimide in dichloromethane (1.0 M, 71 μL, 0.071 mmol). After stirring over night at room temperature, the mixture is diluted with 7:3 ethyl acetate/hexanes and filtered. The filter cake is washed with 7:3 ethyl acetate/hexanes (3×3 mL). The filtrate is concentrated and the residue is chromatographed on silica gel, eluting with 6:4 ethyl acetate/hexanes to provide 10 mg (83%) of N-[tert-butoxycarbonyl]-Cryptophycin-309 as a foam. The foam (5 mg, 0.006 mmol) is dissolved and stirred in dichloromethane (100 μL) and treated with hydrogen chloride (10 μL of a 4.0 M solution in dioxane, 0.04 mmol). After stirring for 1.5 hours at room temperature, the solution is concentrated to provide 4.6 mg (96%) of the title compound as an amorphous solid.

$[\alpha]_D^{20}$=+22.4° (c=2.1, $CH_3OH$).

MS(FAB): m/e (% relative intensity) 762 (100), 726 (4.4), 653 (3.4), 307 (12.4).

MS(HRFAB): m/e=762.2962 (Calculated for $C_{38}H_{50}Cl_2N_3O_9$: 762.2924).

A therapeutically effective amount of a compound of Formula I is expected to vary from about 0.001 milligram per kilogram of body weight per day (mg/kg/day) to about 100 mg/kg/day. Preferred amounts are expected to vary from about 1 to about 100 mg/kg/day.

Cryptophycin-309 and the pharmaceutically acceptable salts thereof are normally administered intravenously, and so intravenous administration is preferred. However, intravenous administration is not the only route or even the only preferred route. Compounds of Formula I may also be administered by the oral, percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences,* 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for intravenous, oral, inhalation, parenteral, or topical use and may be administered to the patient in the form of tablets, capsules, aerosols, inhalants, suppositories, solutions, suspensions, or the like.

The compounds of the present invention may be administered intravenously, for example, as aqueous solutions containing suitable carriers. Suitable carriers are well known to the skilled artisan and include ethanol, Tween-80, solutol, and Cremophor.

The compounds of the present invention may also be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate, disintegrating agents such as: croscarmellose, crospovidone, sodium starch glycolate, corn starch and the like; lubricants such as: magnesium stearate, steric acid, talc or hydrogenated vegetable oil; glidants such as colloidal silicon dioxide; wetting agents such as: sodium lauryl sulfate and polysorbate 80; and sweetening agents such as: sucrose, aspartame or saccharin may be added or a flavoring agent such as: peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

Conventional Murine Tumor and Human Tumor Xenograft Assays

Inhibition of tumors transplanted into mice is an accepted procedure for studying the efficacy of antitumor agents (Corbett, et al., *In vivo Methods for Screening and Preclinical Testing; Use of rodent solid tumors for drug discovery.*, In: Anticancer Drug Development Guide: Preclinical Screening, Clinical Trials, and Approval, B. Teicher (ed), Humana Press Inc., Totowa, N.J., Chapter 5, pages 75–99 (1997); (Corbett, et al., *Int. J. Pharmacog.*, 33, Supplement, 102–122 (1995)). Murine tumors or human xenographs were implanted essentially as described by Corbett in *In vivo Methods for Screening and Preclinical Testing; Use of rodent solid tumors for drug discovery.* Briefly, the murine tumor or human xenograph was implanted subcutaneously using either 12-gauge trocar implants or counted number of cells. The location for the trocar insertion is midway between the axillary and inguinal region along the side of the mouse. The trocar is slipped approximately ¾ of an inch subcutaneously up toward the axilla before discharging the tumor fragment, and pinching the skin as the trocar is removed. Alternatively, human tumor cells prepared from a brie of donor tumors ($5 \times 10^6$ cells) were implanted subcutaneously in a hind-leg of a male or female nude mouse (Charles River). Either a test compound in vehicle or vehicle alone was administered by intravenous bolus injection (iv), intraperitoneal injection (ip), or oral gavage (po). Each treatment group, as well as a group of untreated control animals, consisted of five animals per group in each experiment. Subcutaneous tumor response was monitored by tumor volume measurement performed twice each week over the course of the experiment (60–120 days). Body weights were taken as a general measure of toxicity. The subcutaneous tumor data were analyzed by determining the median tumor weight for each treatment group over the course of the experiment and calculating the tumor growth delay as the difference in days for the treatment versus the control tumors to reach a volume of either 500 or 1000 $mm^3$.

Cryptophycin-309 (309) was tested against a variety of murine and human tumors substantially as described supra. Cryptophycin-55 glycinate (55-GLY), Taxol, and Adriamycin (Adria) were also included in certain tests for purposes of comparison. Cryptophycin 55 glycinate is known in the art (WO 98/08505, Example 9) and has the following structure:

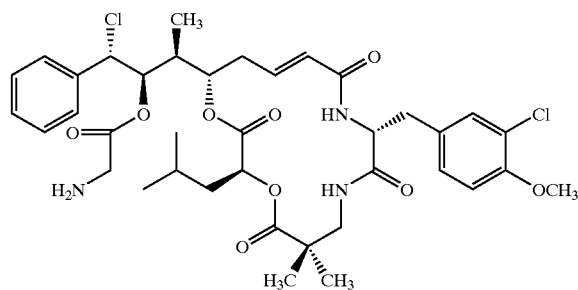

CRYPTOPHYCIN-55-GLYCINATE

The data from these tests are summarized in TABLES I–VIII. The parameters measured in each experiment are summarized in the following paragraphs.

Tumor Weight(mg)=$(a \times b^2)/2$ where a=tumor length (mm) and b=tumor width (mm).

Tumor Growth Delay=T−C where T is the median time (days) required for the treatment group tumors to reach a predetermined size, and C is the median time (days) for the control group tumors to reach the same size. Tumor-free survivors are excluded from this calculation, and are tabulated separately (Tumor Free).

Log Kill=Tumor Growth Delay/(3.32)(Td)

where Tumor Growth Delay is as previously defined and Td is tumor volume doubling time (days), estimated from the best fit straight line from a log-linear growth plot of the control group of tumors in exponential growth (100–800 mg range)

%T/C mass—The treatment and control groups are measured when the control group tumors reach approximately 700 to 1200 mg in size (median group). The median tumor weight of each group is determined (including zeros). The T/C value in percent is an indication of antitumor effectiveness. A T/C≦42% is considered significant antitumor activity. A T/C<10% is considered to indicate highly significant antitumor activity.

Body Weight Loss Nadir—A body weight loss nadir (mean of group) of greater than 20% or drug deaths greater than 20% are considered to indicate an excessively toxic dosage in single course trials.

Activity Rating—the Activity Rating is derived from the Log Kill according to the following table:

| ANTITUMOR ACTIVITY | LOG KILL | ACTIVITY RATING |
|---|---|---|
| HIGHLY ACTIVE | >2.8 | ++++ |
|  | 2.0–2.8 | +++ |
|  | 1.3–1.9 | ++ |
|  | 0.7–1.2 | + |
| INACTIVE | <0.7 | − |

TABLE I

MURINE EARLY STAGE MAMMARY ADENOCARCINOMA-17/ADR/Resist.
(C3H Female Mice, Kingston)

| COMPOUND | TOTAL DOSE (mg/kg) | DRUG DEATHS | MEDIAN TUMOR WEIGHT (mg) | % T/C MASS | GROWTH DELAY (DAYS) | LOG KILL | ACTIVITY RATING |
|---|---|---|---|---|---|---|---|
| Untreated | 0 | — | 2383 | — | — | — | — |
| 309[a] | 150 | 0/5 | 0 | 0% | 10.75 | 3.23 | ++++ |
| 55-GLY[b] | 210 | 0/5 | 0 | 0% | 7.6 | 2.3 | +++ |
| 55-GLY[c] | 140 | 0/5 | 577 | 24% | 5.25 | 1.6 | ++ |

[a]Drug was administered IV at 30 mg/kg/inj on days 1, 3, 5, 7, and 9.
[b]Drug was administered IV at 42 mg/kg/inj on days 1, 3, 5, 7, and 9.
[c]Drug was administered IV at 28 mg/kg/inj on days 1, 3, 5, 7, and 9.

TABLE II

EARLY STAGE MURINE MAMMARY ADENOCARCINOMA-16/C/Adr
(C3H female mice, CRL-Kingston)

| COMPOUND | TOTAL DOSE (mg/kg) | DRUG DEATHS | MEDIAN TUMOR WEIGHT (mg) | % T/C MASS | GROWTH DELAY (DAYS) | LOG KILL | ACTIVITY RATING |
|---|---|---|---|---|---|---|---|
| Untreated | 0 | — | 2304 | — | — | — | — |
| 309[a] | 100 | 0/5 | 0 | 0% | 11 | 3.0 | ++++ |
| 55-GLY[b] | 168 | 0/5 | 0 | 0% | 7.8 | 2.1 | +++ |
| 55-GLY[c] | 140 | 0/5 | 48 | 24% | 6.2 | 1.7 | ++ |
| Adriamycin[d] | 15 | 0/5 | 1096 | — | — | None | — |
| Taxol[e] | 70 | 0/5 | 1198 | — | — | None | — |

[a]Drug was administered IV at 20 mg/kg/inj on days 1, 3, 5, 7, and 9.
[b]Drug was administered IV at 42 mg/kg/inj on days 1, 3, 7, and 9.
[c]Drug was administered IV at 28 mg/kg/inj on days 1, 3, 5, 7, and 9.
[d]Drug was administered IV at 7.5 mg/kg/inj on days 1 and 7.
[e]Drug was administered IV at 10 mg/kg/inj QD 1–7.

TABLE III

EARLY STAGE MURINE COLON ADENOCARCINOMA-26/A
(Balb/C female mice, Kingston)

| COMPOUND | TOTAL DOSE (mg/kg) | DRUG DEATHS | MEDIAN TUMOR WEIGHT (mg) | % T/C MASS | GROWTH DELAY (DAYS) | LOG KILL | ACTIVITY RATING |
|---|---|---|---|---|---|---|---|
| Untreated | 0 | — | 900 | — | — | — | — |
| 309[a] | 175 | 0/5 | 0 | 0% | 15.25 | 2.7 | +++ |
| 309[b] | 115 | 0/5 | 0 | 0% | 12.75 | 2.3 | +++ |
| 309[c] | 75 | 0/5 | 126 | 14% | 6.65 | 1.2 | + |

TABLE III-continued

EARLY STAGE MURINE COLON ADENOCARCINOMA-26/A
(Balb/C female mice, Kingston)

| COMPOUND | TOTAL DOSE (mg/kg) | DRUG DEATHS | MEDIAN TUMOR WEIGHT (mg) | % T/C MASS | GROWTH DELAY (DAYS) | LOG KILL | ACTIVITY RATING |
|---|---|---|---|---|---|---|---|
| Adriamycin[d] | 19.5 | 0/5 | 393 | 44% | — | None | — |
| Taxol[e] | 80 | 0/5 | 516 | 57% | — | None | — |

[a]Drug was administered IV at 35 mg/kg/inj on days 1, 3, 5, 7, and 9.
[b]Drug was administered IV at 23 mg/kg/inj on days 1, 3, 5, 7, and 9.
[c]Drug was administered IV at 15 mg/kg/inj on days 1, 3, 5, 7, and 9.
[d]Drug was administered IV at 6.5 mg/kg/inj on days 1, 5, and 9.
[e]Drug was administered IV at 10 mg/kg/inj QD 1–7, 9.

TABLE IV

MURINE PANCREATIC DUCTAL ADENOCARCINOMA #02
(BDF₁ female mice, NIH Raleigh)

| COMPOUND | TOTAL DOSE (mg/kg) | DRUG DEATHS | MEDIAN TUMOR WEIGHT (mg) | % T/C MASS | GROWTH DELAY (DAYS) | LOG KILL | ACTIVITY RATING |
|---|---|---|---|---|---|---|---|
| #Untreated | 0 | — | 1650 | — | — | — | — |
| ##Untreated | 0 | — | 1059 | — | — | — | — |
| ##309[a] | 165 | 0/5 | 0 | 0% | 15.25 | 2.7 | +++ |
| #309[b] | 150 | 0/5 | 64 | 3.8% | 13 | 1.7 | ++ |
| #309[c] | 100 | 0/5 | 63 | 3.8% | 13 | 1.7 | ++ |
| ##55-GLY[d] | 210 | 0/5 | 0 | 0% | 16 | 2.2 | +++ |
| ##55-GLY[e] | 140 | 0/5 | 95 | 9% | 13 | 1.8 | ++ |
| #Taxol[f] | 64 | 0/5 | 1296 | 79% | 1 | 0.1 | — |

"#" and "##" designate results from separate experiments.
[a]Drug was administered IV at 33 mg/kg/inj on days 1, 3, 5, 7, and 9.
[b]Drug was administered IV at 30 mg/kg/inj on days 1, 3, 5, 7, and 9.
[c]Drug was administered IV at 20 mg/kg/inj on days 1, 3, 5, 7, and 9.
[d]Drug was administered IV at 42 mg/kg/inj on days 1, 3, 5, 7, and 9.
[e]Drug was administered IV at 28 mg/kg/inj on days 1, 3, 5, 7, and 9.
[f]Drug was administered IV at 8 mg/kg/inj QD 1–8.

TABLE V

EARLY STAGE MURINE COLON ADENOCARCINOMA 51/A
(CDF female mice, Kingston)

| COMPOUND | TOTAL DOSE (mg/kg) | DRUG DEATHS | MEDIAN TUMOR WEIGHT (mg) | % T/C MASS | GROWTH DELAY (DAYS) | LOG KILL | ACTIVITY RATING |
|---|---|---|---|---|---|---|---|
| Untreated | 0 | — | 1138 | — | — | — | — |
| 309[a] | 140 | 0/6 | 0 | 0% | 20.1 | 2.4 | +++ |
| Adriamycin[b] | 19.5 | 0/6 | 0 | 0% | 16.6 | 2.0 | +++ |
| Taxol[c] | 80 | 0/6 | 288 | 25% | 5.6 | 0.7 | + |

[a]Drug was administered IV at 28 mg/kg/inj on days 3, 5, 7, 9, and 11.
[b]Drug was administered IV at 6.5 mg/kg/inj on days 3, 6, and 9.
[c]Drug was administered IV at 10 mg/kg/inj QD 1–8.

TABLE VI

MURINE UPSTAGED MAMMARY ADENOCARCINOMA 16/C
(C3H/HeN female mice, NIH Kingston)

| COMPOUND | TOTAL DOSE (mg/kg) | DRUG DEATHS | MEDIAN TUMOR WEIGHT (mg) | % T/C MASS | GROWTH DELAY (DAYS) | LOG KILL | ACTIVITY RATING |
|---|---|---|---|---|---|---|---|
| Untreated | 0 | — | 1251 | — | — | — | — |
| 309[a] | 150 | 0/5 | 0 | 0% | 16.5 | 3.8 | ++++ |
| 309[b] | 100 | 0/5 | 0 | 0% | 17 | 3.9 | ++++ |
| 55-GLY[c] | 210 | 0/5 | 0 | 0% | 17.5 | 4.1 | ++++ |

TABLE VI-continued

MURINE UPSTAGED MAMMARY ADENOCARCINOMA 16/C
(C3H/HeN female mice, NIH Kingston)

| COMPOUND | TOTAL DOSE (mg/kg) | DRUG DEATHS | MEDIAN TUMOR WEIGHT (mg) | % T/C MASS | GROWTH DELAY (DAYS) | LOG KILL | ACTIVITY RATING |
|---|---|---|---|---|---|---|---|
| 55-GLY[d] | 140 | 0/5 | 0 | 0% | 15 | 3.5 | ++++ |
| Taxol[e] | 72 | 0/5 | 0 | 0% | 12.5 | 2.9 | ++++ |

[a]Drug was administered IV at 30 mg/kg/inj on days 3, 5, 7, 9, and 11.
[b]Drug was administered IV at 20 mg/kg/inj on days 3, 5, 7, 9, and 11.
[c]Drug was administered IV at 42 mg/kg/inj on days 3, 5, 7, 9, and 11.
[d]Drug was administered IV at 28 mg/kg/inj on days 3, 5, 7, 9, and 11.
[e]Drug was administered IV at 8 mg/kg/inj QD 3–11.

TABLE VII

EARLY STAGE HUMAN COLON ADENOCARCINOMA 15
(Balb/C SCID female mice, NIH)

| COMPOUND | TOTAL DOSE (mg/kg) | DRUG DEATHS | MEDIAN TUMOR WEIGHT (mg) | % T/C MASS | GROWTH DELAY (DAYS) | LOG KILL | ACTIVITY RATING |
|---|---|---|---|---|---|---|---|
| Untreated | 0 | — | 1139 | — | — | — | — |
| 309[a] | 190 | 0/5 | 0 | 0% | 32.5 | 3.3 | ++++ |
| 309[b] | 125 | 0/5 | 0 | 0% | 31.5 | 3.2 | ++++ |
| 309[c] | 82.5 | 0/5 | 126 | 11% | 24.5 | 2.5 | +++ |
| 55-GLY[d] | 320 | 0/5 | 0 | 0% | 56 | 4.0 | ++++ |
| 55-GLY[e] | 210 | 0/5 | 63 | 5.5% | 21.5 | 2.2 | +++ |
| 55-GLY[f] | 140 | 0/5 | 171 | 15% | 21.5 | 2.2 | +++ |
| Taxol[g] | 85.5 | 0/5 | 1044 | 67% | 3.5 | 0.4 | — |

[a]Drug was administered IV at 38 mg/kg/inj on days 3, 5, 7, 9, and 11.
[b]Drug was administered IV at 25 mg/kg/inj on days 3, 5, 7, 9, and 11.
[c]Drug was administered IV at 16.5 mg/kg/inj on days 3, 5, 7, 9, and 11.
[d]Drug was administered IV at 32 mg/kg/inj on twice/day on days 3, 5, 7, 9, and 11.
[e]Drug was administered IV at 42 mg/kg/inj on days 3, 5, 7, 9, and 11.
[f]Drug was administered IV at 28 mg/kg/inj on days 3, 5, 7, 9, and 11.
[g]Drug was administered IV at 9.5 mg/kg/inj QD 3–11.

TABLE VIII

EARLY STAGE HUMAN COLON ADENOCARCINOMA HCT-116
(Balb/C SCID female mice, NIH)

| COMPOUND | TOTAL DOSE (mg/kg) | DRUG DEATHS | MEDIAN TUMOR WEIGHT (mg) | % T/C MASS | GROWTH DELAY (DAYS) | LOG KILL | ACTIVITY RATING |
|---|---|---|---|---|---|---|---|
| Untreated | 0 | — | 1146 | — | — | — | — |
| 309[a] | 190 | 0/5 | 0 | 0% | 34 | 4.1 | ++++ |
| 309[b] | 125 | 0/5 | 0 | 0% | 29.5 | 3.6 | ++++ |
| 309[c] | 82.5 | 0/5 | 0 | 0% | 22 | 2.65 | +++ |
| 55-GLY[d] | 320 | 0/4 | 0 | 0% | 35 | 4.2 | ++++ |
| 55-GLY[e] | 210 | 0/5 | 0 | 0% | 25 | 3.0 | ++++ |
| 55-GLY[f] | 140 | 0/5 | 63 | 5.5% | 22 | 2.65 | +++ |
| Taxol[g] | 72 | 0/5 | 126 | 11% | 17 | 2.0 | +++ |

[a]Drug was administered IV at 38 mg/kg/inj on days 3, 5, 7, 9, and 11.
[b]Drug was administered IV at 25 mg/kg/inj on days 3, 5, 7, 9, and 11.
[c]Drug was administered IV at 16.5 mg/kg/inj on days 3, 5, 7, 9, and 11.
[d]Drug was administered IV at 32 mg/kg/inj on twice/day on days 3, 5, 7, 9, and 11.
[e]Drug was administered IV at 42 mg/kg/inj on days 3, 5, 7, 9, and 11.
[f]Drug was administered IV at 28 mg/kg/inj on days 3, 5, 7, 9, and 11.
[g]Drug was administered IV at 9 mg/kg/inj QD 3–10.

We claim:
1. A compound of the Formula I:

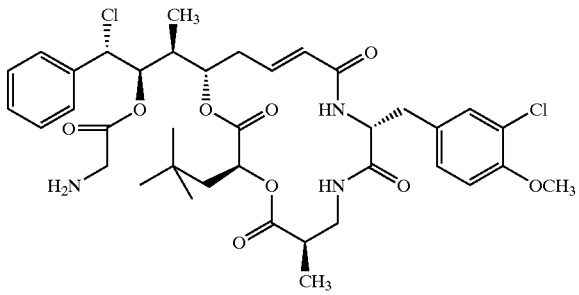

or a pharmaceutically acceptable salt thereof.

2. A compound of claim 1, wherein the compound is a pharmaceutically acceptable salt of a compound of Formula I.

3. A compound of claim 2, wherein the pharmaceutically acceptable salt is the hydrochloride salt.

4. A pharmaceutical formulation comprising a pharmaceutically acceptable carrier, diluent or excipient in combination with a compound of Formula I:

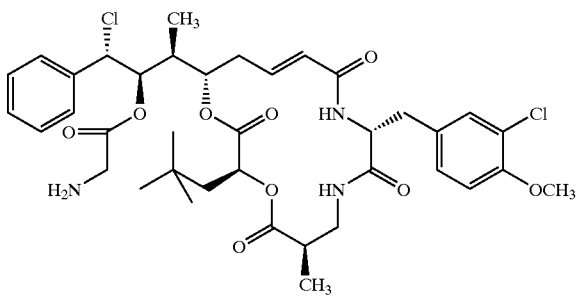

or a pharmaceutically acceptable salt thereof.

5. A formulation of claim 4, wherein the compound is a pharmaceutically acceptable salt of a compound of Formula I.

6. A formulation of claim 5, wherein the pharmaceutically acceptable salt is the hydrochloride salt.

7. A method for the treatment of a susceptible neoplasm in mammals comprising administering to a mammal in need of such treatment a pharmaceutically effective amount of the compound of Formula I:

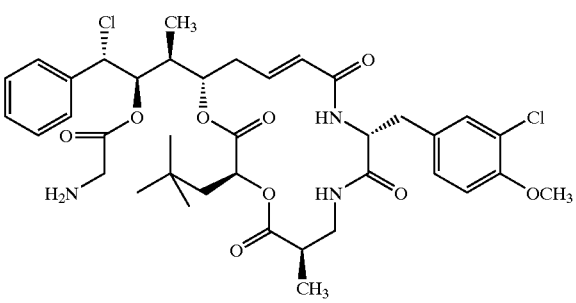

or a pharmaceutically acceptable salt thereof.

8. A method of claim 7, wherein the compound is a pharmaceutically acceptable salt of a compound of Formula I.

9. A method of claim 8, wherein the pharmaceutically acceptable salt is the hydrochloride salt.

* * * * *

UNITED STATES PATENT AND TRADEMARK OFFICE
CERTIFICATE OF CORRECTION

PATENT NO. : 6,747,021 B2
APPLICATION NO. : 09/915638
DATED : June 8, 2004
INVENTOR(S) : Corbett et al.

It is certified that error appears in the above-identified patent and that said Letters Patent is hereby corrected as shown below:

Front page, (73) Assignees: "Eli Lilly and Company, Indianapolis, IN (US); Wayne State University, Detroit, MI (US); University of Hawaii, Honolulu, HI (US)" should read --Wayne State University, Detroit, MI (US); University of Hawaii, Honolulu, HI (US)--

Signed and Sealed this

Fifth Day of December, 2006

JON W. DUDAS
*Director of the United States Patent and Trademark Office*